United States Patent [19]

Schäl

[11] 4,108,575

[45] Aug. 22, 1978

[54] OBTAINING DESIRED FLOW RATE FROM ROLLER PUMP DESPITE VARYING THE HOSE MEANS

[75] Inventor: Wilfried Schäl, Bad Homburg-Dornholzhausen, Fed. Rep. of Germany

[73] Assignee: Dr. Eduard Fresenius Chemisch-pharmazeutische Industrie K.G., Bad Homburg, Fed. Rep. of Germany

[21] Appl. No.: 692,373

[22] Filed: Jun. 3, 1976

[30] Foreign Application Priority Data

Aug. 9, 1975 [DE] Fed. Rep. of Germany ....... 2535650

[51] Int. Cl.² ...................... F04B 43/08; F04B 43/12; F04B 45/06
[52] U.S. Cl. .................................. 417/53; 417/475; 417/477; 128/DIG. 13
[58] Field of Search ................ 417/477, 43, 475, 53; 128/DIG. 13; 235/184

[56] References Cited

U.S. PATENT DOCUMENTS

| | | | |
|---|---|---|---|
| 3,415,419 | 12/1968 | Jewett et al. | 417/477 |
| 3,428,788 | 2/1969 | Fisher et al. | 235/184 |
| 3,502,034 | 3/1970 | Pickup | 417/477 |
| 3,582,234 | 6/1971 | Isreeli et al. | 417/477 |
| 3,935,971 | 2/1976 | Papoff et al. | 417/426 |

OTHER PUBLICATIONS

Reque, "Simulate the System with an Analog Computer," Control Engineering, Sep. 1956, pp. 138–144.

*Primary Examiner*—Carlton R. Croyle
*Assistant Examiner*—Thomas I. Ross
*Attorney, Agent, or Firm*—W. G. Fasse; W. W. Roberts

[57] ABSTRACT

A roller pump having one or more hoses is combined with a control system including a potentiometer for controlling the speed of the pump motor. A manually settable control provides an output corresponding to the diameter of the hose, and a further control provides an output corresponding to the number of hoses. An electronic circuit connected to receive the outputs of the controls, provides an output signal corresponding to the flow rate of the pump. This signal is applied to an indicator, so that an operator may adjust the speed of the pump to obtain a desired flow rate.

2 Claims, 7 Drawing Figures

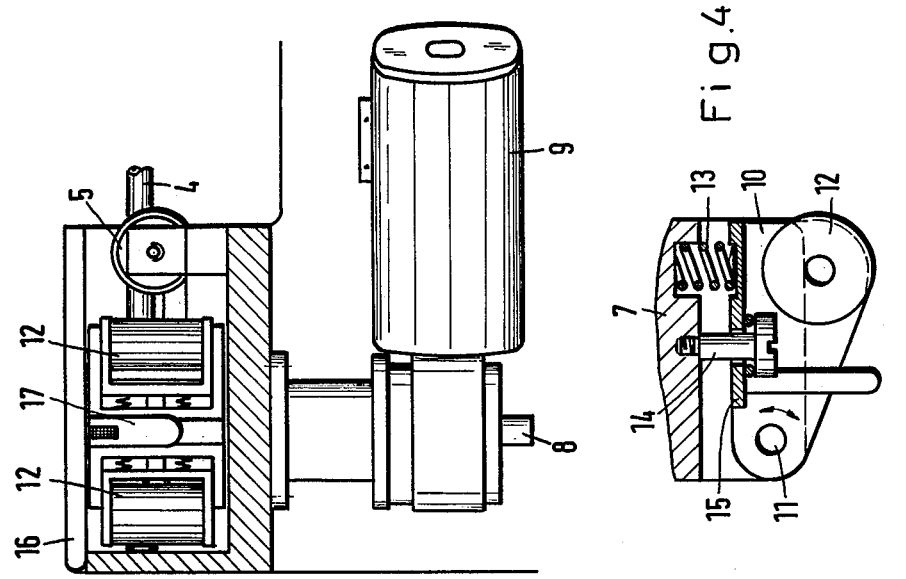

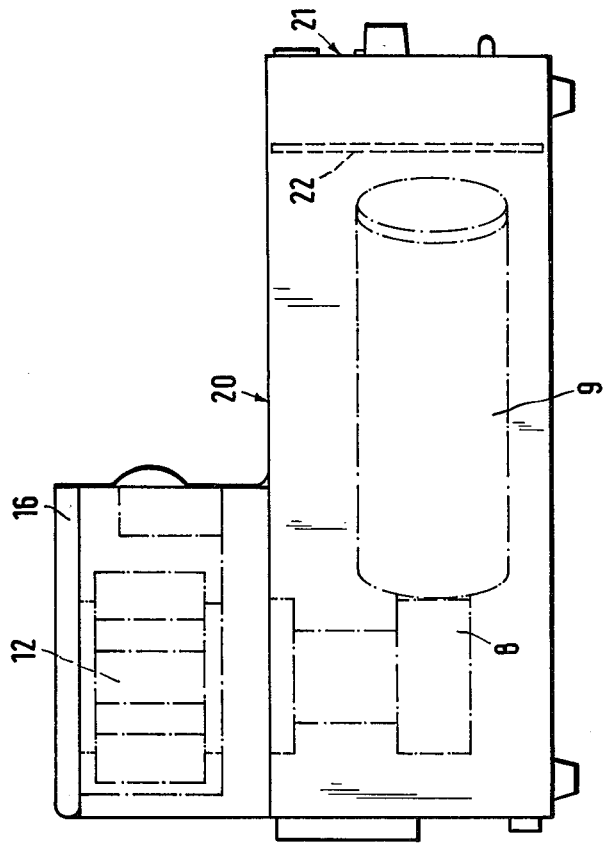
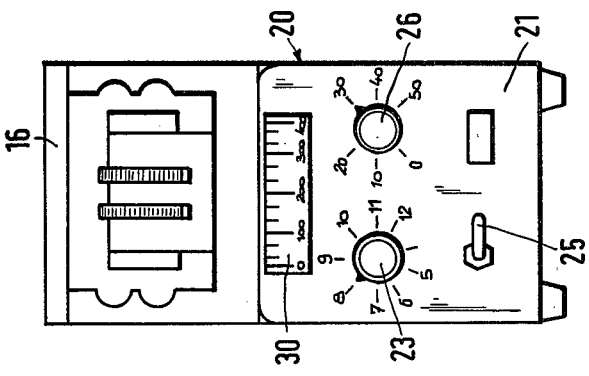

OBTAINING DESIRED FLOW RATE FROM ROLLER PUMP DESPITE VARYING THE HOSE MEANS

BACKGROUND OF THE INVENTION

This invention relates to roller pump systems, and is particularly directed to the provision of a roller pump having calibrating and/or indicating means for determining or controlling the flow rate of the pump.

Such devices are preferably used for treatment with an artificial kidney or an artificial heart and lung.

Devices of this type have been known in various designs. In medical applications, one or two pump hoses are inserted in a stator having an open side so that the hoses are bent by 180°. A central rotor adjustable for use with two or three rollers is fixed in the stator.

The rollers press the hose or hoses against the stator wall in such a way that the hose cross section is closed at the pressure point.

When the rotor is turned the medium in the hose or hoses is transported in direction of the rotation of the rotor.

Hose systems used for extra-corporal circuits are made with different diameters and different wall thicknesses and of different materials. For conventional roller pumps it is therefore necessary that the spacing between the stator and the rotor rollers be precisely adjusted according to the dimensions of the hose or hoses used.

For the treatment it is important to maintain a definite delivery rate per time unit in order not to endanger the patient.

OBJECT OF THE INVENTION

The purpose of the invention is to avoid overloading the personnel, or in case of home treatment the patient, by using a device as described above, and to provide a direct means of indication of the flow rate per time unit.

SUMMARY OF THE INVENTION

To solve this problem in a device as described above the invention comprises a circuit for adjusting the pump speed, for adjustment of input variables such as the hose cross section and number of hoses, and for indication of the flow rate per time unit.

Further features of the invention are the special design of the circuitry, i.e., a calculating circuit and a control circuit for the pump motor.

The further features of the invention are the design of this circuitry and its interconnections.

The features of advantage for the invention are described in the claims.

BRIEF FIGURE DESCRIPTION

One realization of the subject of the invention is schematically shown in the drawing as an example, wherein:

FIG. 1: Top view of a pump head
FIG. 2: Section II—II of FIG. 1.
FIG. 3: Section III—III of FIG. 1.
FIG. 4: Detail of a portion of FIG. 1 with increased scale.
FIG. 5: Front view of a device according to the invention.
FIG. 6: Lateral view of a device according to the invention.
FIG. 7: Block diagram of a circuitry according to the invention.

DETAILED DESCRIPTION OF PREFERRED EXAMPLE EMBODIMENTS

Figure 7:
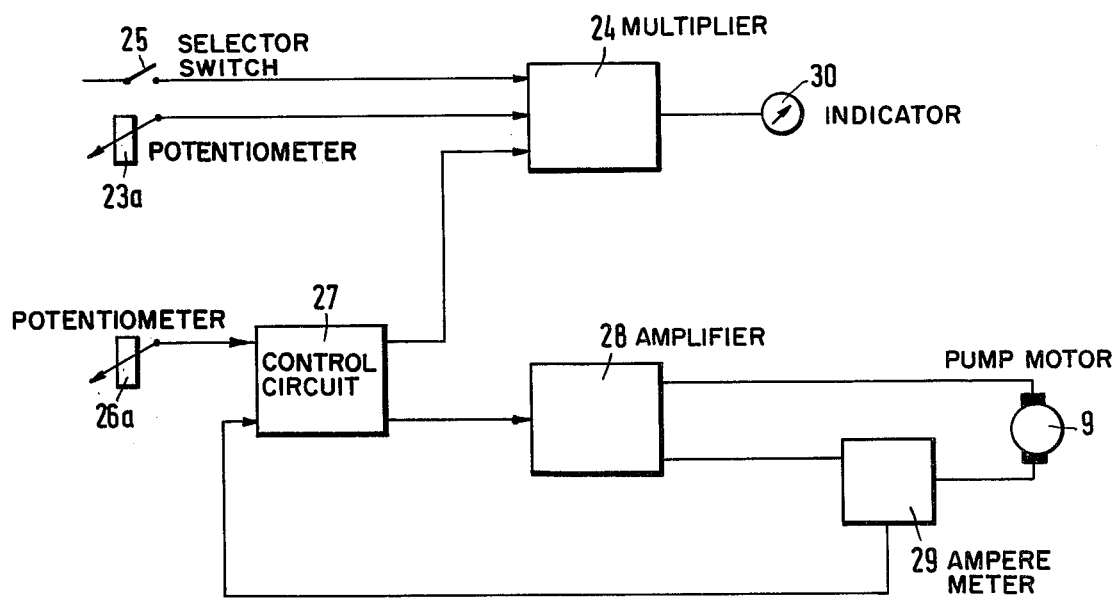

According to the drawings, two guide grooves 2, 3 are arranged at the inside of stator 1 each of which is adapted to accommodate a separate hose 4 (only one of which is shown).

The hose 4 thus is bent 180° by insertion in the guide grooves 2 or 3 of the stator 1. Clamps 6 for fixing the hose 4 in the stator 1 are arranged at the open end of the stator 1 for operation by means of thumb screws 5.

FIG. 1 shows the clamps 6 prior to clamping the hose ends.

The rotor 7 is arranged in the middle of the stator 1. Rotor 7 is rotated about its axis 8 by a d.c. gear motor 9.

Two identical levers 10 are pivotally mounted on the rotor for rotation about separate axes 11.

Each of the levers 10 carry a separate roller 12.

The levers 10 are pressed radially outwards by separate pre-tensioned helical spring 13. The swivelling path of each lever is limited by a stop screw 14 (FIG. 4). The stop screw 14 is screwed into the rotor 7 and passes freely through a hole into the inner side wall 15 of the swivelling lever 10.

On insertion of one or two pump hoses 4 into the stator 1 the rollers 12 adapt themselves elastically to the hose diameter concerned. The helical spring 13 are pre-tensioned so that all hoses suitable for the purpose can be safely pressed off without being overloaded.

In order to enable inserting the pump hoses after removing the cover 16 the rotor 7 can be rotated with the manual crank 17 shown in folded condition.

For unfolding the hand crank 17, the coupling between the rotor shaft 8 and the gear motor 9 is simultaneously released by conventional means.

Moreover means can be provided to make sure that the motor 9 can run only with closed cover 16.

The described design enables the use of different hose systems without any mechanical adjustment.

The above described design of a device for conveying a liquid in hose systems is arranged in an outer housing 20 whose front side 21 is provided e.g., with adjustment devices to which a circuit 22 is connected for adjustment of the pump speed, for adjustment of an input value corresponding to hose cross section and the number of hoses in use for indication of the flow rate. A meter 30 per time unit is also provided in the side 21.

This circuitry is schematically shown on FIG. 7 in the form of a block diagram which is described in more detail as follows:

The front plate comprises the adjustment knob 23 which may be selectively set to positions corresponding the hose diameter $d$ of the hoses inserted in the hose pump as indicated by the adjacent dial on the side 21. This adjustment device is connected with a potentiometer 23a which is in turn connected with a calculation circuit 24, for example in the form of an analog computer. This calculation circuitry 24 determines the value $d^2 \pi/4$. The value $\pi/4$ is contained therein as constant and the value $d$ which is adjusted by the knob 23 is squared in this calculation circuitry.

A further adjustment device 25 shown in the example as a switch, is also connected to the calculation circuitry 24 to provide a manually adjustable input corresponding to the number of hoses inserted in the hose pump.

A switching device 26 serves to adjust the pump speed per time unit and for this purpose it is mounted adjacent an appropriate scale. This adjustment device actuates a potentiometer 26 a in the circuitry 22. The voltage set at this potentiometer acts on a control circuit 27 for adjustment and maintaining the speed of the pump motor 9. A power amplifier 28 is connected in series with the control circuit 27 to supply the operating current for the pump motor 9 which for example can be a d.c. motor.

An ammeter 29 is connected in the power circuit of the pump motor 9 to supply a switching signal for the control circuit 27 via its output. In this way a linear relation between motor speed and the set specified value of this speed is obtained independent of the load.

One output of the control circuit 27 is also connected to the calculation circuit 24.

In the calculation circuit 24 an indicating value is determined from the input parameters, i.e. the number of inserted hoses, the cross section of the inserted hoses and the set pump speed. This indication value is transmitted to the indicating unit 30. The scale of the indicating unit 30 is calibrated directly in units of the flow rate per time unit. Thus it is possible by changing the setting of the pump speed, to exactly adjust the pump for a desired flow rate at the adjustment device 26.

The invention therefore enables the use of different hose systems. In this connection the continuous indication of the flow rate for each hose system is therefore a particular advantage. It is possible for the operating personnel, the physician in charge or even the patient to adjust and if necessary to correct for the most favorable value of the flow rate specified for the treatment concerned.

Referring specifically to FIG. 7 the operation will now be described. It is assumed that the desired number of tubes has been inserted in the pump, and that the diameter of the tubes is known. The knob 23 is set manually to the scale marking indicating this known diameter of the tubes, and the control switch 25 is set manually to the position corresponding to the number of tubes in the pump. Thus, voltages corresponding to these two parameters are applied to the calculating circuit 24. In one mode of operation, the knob 26 is then controlled, to apply a further voltage to the calculation circuit by adjusting the potentiometer 26a through the knob 26 until the indicator 30 shows the desired flow rate due to the fact that the potentiometer 26a controls the operating voltage applied by the amplifier 28 to the pump motor 9.

In another mode of operation, the knob 26 may be set to a desired scale setting as shown in FIG. 5, corresponding to a predetermined speed of rotation of the motor. In any event, the meter 30 will indicate the resultant flow rate because one output of the control circuit 27 is also connected to the calculating circuit 24.

Since the flow rate depends on the number of hoses, on the cross-sectional flow area, or on the inner diameter of the hoses, and on the speed of the motor, a simple calculating circuit 24 may be employed, such as a conventional analog multiplier, preferably a semiconductor chip having this function.

The invention is not limited to the explained and described example. The circuitry of the invention can readily by replaced by other known circuitry components. Nor is it necessary to arrange the indicating unit as a scale instrument, but a direct digital indication can be used.

I claim:

1. A method for operating a peristaltic roller pump so as to maintain a constant delivery rate of blood to a delivery port of an external blood circulatory system despite use of hose types of different diameters in the pump comprising the steps of: providing a first electrical signal representing the number of hoses used, providing a second electrical signal representing the diameter of the hose used, providing a third electrical signal representing the speed of a motor driving said roller pump, supplying said first, second and third electrical signals to analog computer means for calculating a flow rate representing signal from said first, second, and third electrical signals, displaying said flow rate representing signal, adjusting the motor speed signal in accordance with the displayed flow rate in order to obtain indication of a desired flow rate, and supplying the adjusted motor speed signal to the drive motor for driving said pump to produce the desired flow rate.

2. The method of claim 1 further comprising the step of providing a feedback control for operating said drive motor in accordance with a linear response characteristic relative to said third electrical signal representing the motor speed.

* * * * *